United States Patent [19]
Antonacci et al.

[11] Patent Number: 5,368,574
[45] Date of Patent: Nov. 29, 1994

[54] PERCUTANEOUS CATHETER INTRODUCER

[75] Inventors: Anthony C. Antonacci, Pelham Manor, N.Y.; Robert C. Uschold, Cincinnati, Ohio; Crystal C. Sorenson, Blue Ash, Ohio; Kevin J. Bailey, Loveland, Ohio; Kevin D. Duffy, Cincinnati, Ohio

[73] Assignee: Ethicon, Inc., Cincinnati, Ohio

[21] Appl. No.: 955,102

[22] Filed: Oct. 1, 1992

[51] Int. Cl.⁵ .......................... A61M 5/178
[52] U.S. Cl. ................................ 604/164
[58] Field of Search ............ 604/164, 117, 165, 167, 604/272, 274, 264, 268

[56] References Cited

U.S. PATENT DOCUMENTS

| | | | |
|---|---|---|---|
| 1,213,001 | 1/1917 | Philips | 604/117 X |
| 2,091,438 | 8/1937 | Epstein | 604/117 |
| 2,198,666 | 4/1940 | Gruskin | 604/117 |
| 2,361,908 | 11/1944 | Baters | 604/104 |
| 3,039,468 | 6/1962 | Price | 604/164 X |
| 4,243,034 | 1/1981 | Brandt . | |
| 4,613,329 | 9/1986 | Bodicky . | |
| 5,062,836 | 11/1991 | Wendell | 604/164 |
| 5,104,381 | 4/1992 | Gresl et al. . | |
| 5,156,596 | 10/1992 | Balbierz et al. | 604/264 X |
| 5,176,647 | 1/1993 | Knoepfler | 604/158 |
| 5,183,470 | 2/1993 | Wettermann | 604/281 |

FOREIGN PATENT DOCUMENTS

| | | | |
|---|---|---|---|
| 344907 | 12/1989 | European Pat. Off. | 604/167 |
| 9011103 | 10/1990 | WIPO | 604/264 |

OTHER PUBLICATIONS

Article entitled, "A Simple Method for Laparoscopic Cholangiography" (CJS, vol. 35, No. 2, Apr. 1992).
Article entitled, "Laparoscopic Operative Cholangiography: A Simple, Successful, Cost Effective Method", Annals of the Royal College of Surgeons of England (1992) vol. 74, 252–253.
Brochure entitled, "Protectiv I.V. Catheter Safety System" of Critikon, Inc. 1991.
Brochure entitled, "The Critikon I.V. Catheter Line" of Critikon, Inc. 1989.
Brochure entitled, "Ranfac Laparoscopic Cholangiocath", Jan. 1991.
Article entitled, "A New Technique of Laparoscopic Cholangiography", Journal of Laparoendoscopic Surgery, vol. 2, No. 2, 1992.
Applied Vascular Brochure, 1991 (2 pages).
Arrow International, Inc. Brochure, 1991 (1 page).

*Primary Examiner*—Thomas Price
*Attorney, Agent, or Firm*—Dressler, Goldsmith, Shore & Milnamow, Ltd.

[57] ABSTRACT

A percutaneous catheter introducer having a tube with tube handle, a seal housing containing a seal, and a needle with a needle handle. The needle is extended through the seal housing and tube. The needle and tube are percutaneously inserted into an anatomical body cavity. The needle is removed and a catheter is inserted. The seal housing can be removed in order to use the tube for aspiration. Alternatively, the seal is positioned within the tube handle.

17 Claims, 7 Drawing Sheets

PERCUTANEOUS CATHETER INTRODUCER

FIELD OF THE INVENTION

The method and apparatus of this invention relates generally to surgical methods and devices, and more particularly, to a method and apparatus for percutaneous catheter introduction into an anatomical body cavity or into a cystic duct for performing a cholangiogram.

BACKGROUND OF THE INVENTION

In the field of percutaneous catheter introduction, there are a variety of known methods and apparatuses for percutaneous catheter introduction .into an anatomical body cavity.

One known method uses a rigid metal catheter such as the RANFAC ® laparoscopic cholangiocath manufactured by Ranfac Corp., Avon Industrial Park, P.O. Box 635, Avon, Mass. 02322. The metal catheter is inserted through an existing needle hole in the abdomen. This method is discussed in an article entitled "A New Technique of Laparoendoscopic Cholangiography," written by Kenneth D Hagan, M.D., et al. and published in *The Journal of Laparoscopic Surgery*, Volume 2, Number 2, 1992 by Mary Ann Liebert, Inc. The method does not use an introducer sheath or a cannula.

Another procedure for percutaneous catheter introduction is the insertion of a short catheter and introducer needle. The introducer needle is extended through the catheter and protrudes from the distal end of the catheter. The catheter and needle are inserted into the body cavity and the needle is removed from the proximal end of the catheter. The catheter has a coupling means at its proximal end for connecting to a hose, syringe, or other fluid supply means. An example of such a catheter having a seal which may be manually adjusted to close around an introducer needle inserted therein or to close the catheter completely is described in U.S. Pat. No. 4,243,034. The disclosed device does not include a separate introducer sheath for introducing the catheter.

Another procedure for percutaneous catheter introduction is the insertion into a blood vessel of a hollow IV catheter and introducer needle. The IV catheter is connected to a supply of fluids through a luer fitting or other detachable connection. The CRITIKON I.V. catheters manufactured by Critikon, Inc., 4110 George Road, Tampa, Fla. 33631 exemplify such IV catheters and introducer needles. This method also does not use a separate introducer sheath or a separate cannula.

There are certain known methods of percutaneous catheter introduction that include usage of an introducer sheath or cannula and a catheter inserted therein. In these methods generally, a needle is extended through a sheath. The needle and sheath are then inserted percutaneously by being driven through the skin to the desired location within the body cavity. The needle is withdrawn from the sheath and the catheter is inserted into the sheath. An example of this method and an accompanying apparatus is described in U.S. Pat. No. 4,613,329.

In these known methods that use an introducer sheath or cannula, there are certain variations. One known variation includes use of an IV catheter and a rigid metal catheter such as the RANFAC ® laparoscopic cholangiocath discussed above. The IV catheter is inserted into the abdomen in a position to gain access to the cystic duct. The catheter needle is removed and the luer fitting is cut off, leaving a tube providing access to the abdominal cavity. The rigid metal catheter is then inserted into and extended through the IV catheter. The distal tip of the metal catheter is inserted into the cystic duct.

Another variation uses a metal catheter and introducer sheath and needle manufactured by Applied Vascular Devices, Inc., 26051 Merit Circle, Building 104, Laguna Hills, Calif. 92653. The metal catheter includes a rubber seal which snaps over the proximal end of the introducer sheath to prevent loss of pneumoperitoneum.

Another variation is described in an article entitled "Laparoscopic operative cholangiography: a simple, successful, cost effective method," written by Louis J. Fligelstone, et al., and published in the *Annals of the Royal College of Surgeons* of England (1992) vol 74, 252-253. The described method includes insertion of a needle and introducer cannula called a Vygon Dramcath ® (Vygon (UK) Ltd., Bridge Road, Cirencester, Gloucestershire). The needle and introducer cannula are inserted into the abdominal cavity. The needle is removed and a rubber seal is placed over the luer lock. A catheter is then passed through the rubber seal and through the introducer cannula.

The disadvantage of the above methods and apparatuses that use introducer sheaths or cannulas is that fluids and gases may leak from the abdominal cavity through the lumen in the sheath when the sheath and needle are inserted into the abdomen and when the needle is withdrawn from the sheath while the sheath remains inserted in the abdomen. This undesirable leakage occurs when abdominal fluids and/or gases enter the tip of the lumen in the sheath, travel proximally in the lumen, and escape through the proximal end of the lumen outside of the abdominal cavity. When the needle is withdrawn from the sheath, this leakage can be exacerbated. It would be desirable to provide a means for sealing the sheath and needle to prevent such leakage. Further, it would be desirable to provide a means for using the introducer sheath for aspiration of fluids.

Another disadvantage of the above known methods and apparatuses is that the introducer sheath does not sufficiently guide a flexible catheter to the cystic duct. It would be desirable to provide an improved apparatus for guiding a flexible catheter to the cystic duct.

Another disadvantage of the above known methods that use an introducer sheath or cannula is that the depth of insertion of the sheath into the body cavity may be unintentionally increased. Also, after insertion, the angle of insertion may be unintentionally changed by inadvertent movement or jarring of the sheath. It would be desirable to adjustably anchor the sheath to prevent inadvertent increases in the depth of insertion and to prevent unintentional changes in the angle of insertion.

SUMMARY OF THE INVENTION

The percutaneous catheter introducer in accordance with the invention includes a tube defining a lumen for guiding a catheter therethrough. The tube is percutaneously insertable into an anatomical body cavity. A needle is extendable through the tube. A seal housing is detachably connected to the tube. A seal is positioned within the seal housing for sealing the tube against leakage out of its proximal end as the needle is extended through the seal and after the needle is removed from the seal. The seal permits penetration of the needle so as to make a relatively small aperture therein. The aperture is substantially closed as the needle is removed therefrom. The aperture permits insertion of the catheter therethrough.

An adjustable anchor is connected to the tube for preventing inadvertent increases in the depth of insertion of the tube and preventing unintentional changes in the angle of insertion. The anchor is adjustable between an anchored configuration wherein it is affixed to the tube and a non-anchored configuration wherein it is longitudinally slidable along the length of the tube. Preferably, the anchor includes a plurality of feet extending radially outward.

In an alternative embodiment according the invention, the seal has a pre-cut central aperture and radially-extending slits.

In an alternative embodiment according to the invention, a tube handle is connected to the proximal end of the tube and a seal is positioned in the tube handle.

A method for percutaneous insertion of a catheter into a cystic duct in accordance with the invention includes the following steps:
  a) providing a tube for guiding a catheter, said tube having a proximal end and a lumen;
  b) providing a retractable needle extending into the tube;
  c) percutaneously inserting said tube and needle into the abdominal body cavity containing the cystic duct and then removing said needle;
  d) positioning said tube near the cystic duct;
  e) extending said catheter through said lumen and into said cystic duct;
  f) providing a seal associated with the tube for substantially sealing said tube against leakage out of said proximal end of said tube as said needle and catheter are extended through said seal and after said needle and catheter are removed from said seal;
  g) stabilizing the catheter within the cystic duct;
  h) injecting radiopaque contrast medium into the cystic duct; and
  i) adjustably anchoring said tube so as to maintain the angle of insertion.

Preferably, the method includes adjustably anchoring the tube so as to prevent inadvertent increases in the depth in the body cavity.

BRIEF DESCRIPTION OF THE DRAWINGS

A more complete appreciation of this invention, and many of the attendant advantages thereof will be readily apparent as the same becomes better understood by reference to the following detailed description, when considered in conjunction with the accompanying drawings, in which like reference numerals indicate the same or similar components, wherein.

DETAILED DESCRIPTION OF THE INVENTION

The following is a detailed description of the invention and its preferred embodiments. This description is not intended to be an exhaustive description of all embodiments within the scope of the claims and is not intended to limit the scope of the claimed invention to the disclosed embodiments. Modifications and variations will be apparent to those skilled in the art.

Figure 1:
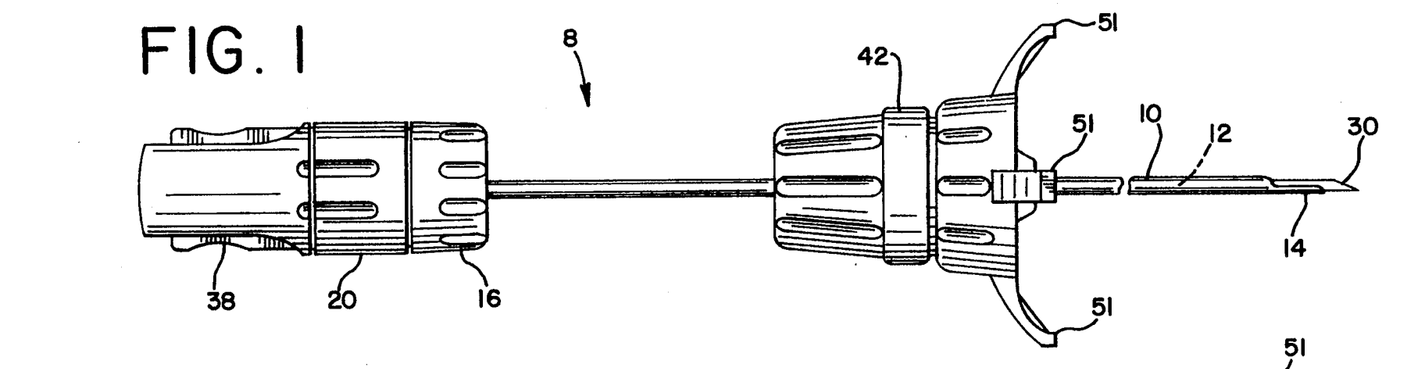
FIG. 1 is an elevational view of the percutaneous catheter introducer in accordance with the invention.
Figure 2:
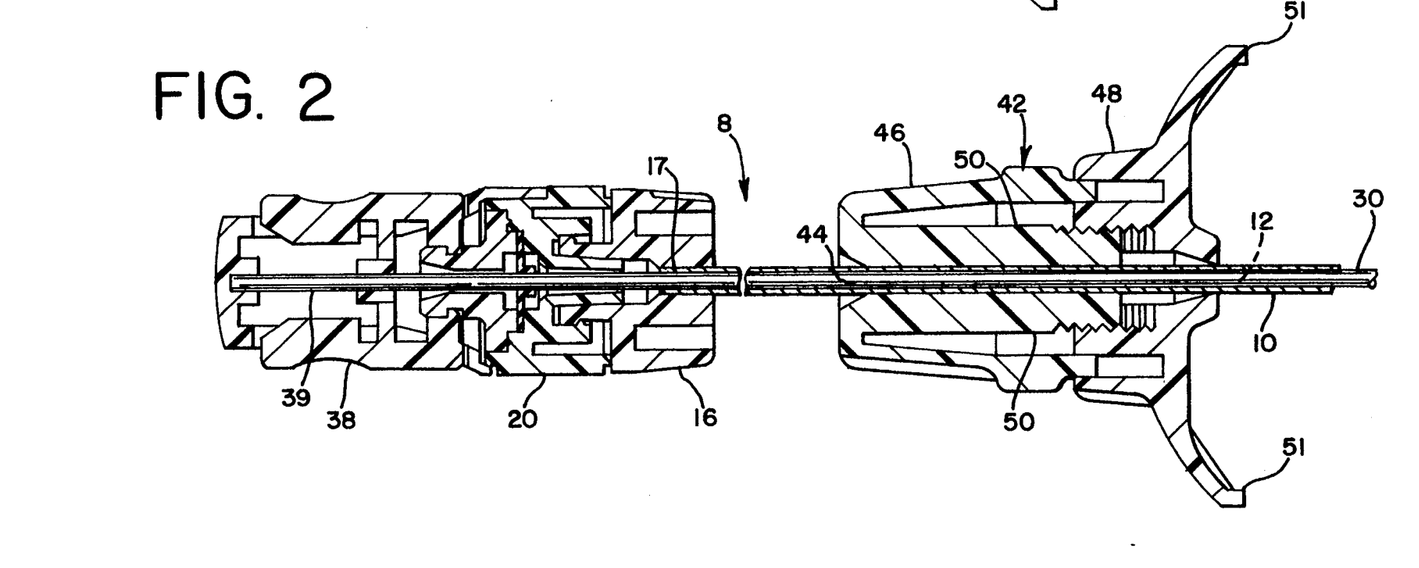
FIG. 2 is a cross-sectional view of the percutaneous catheter introducer in accordance with the invention.
Figure 6:
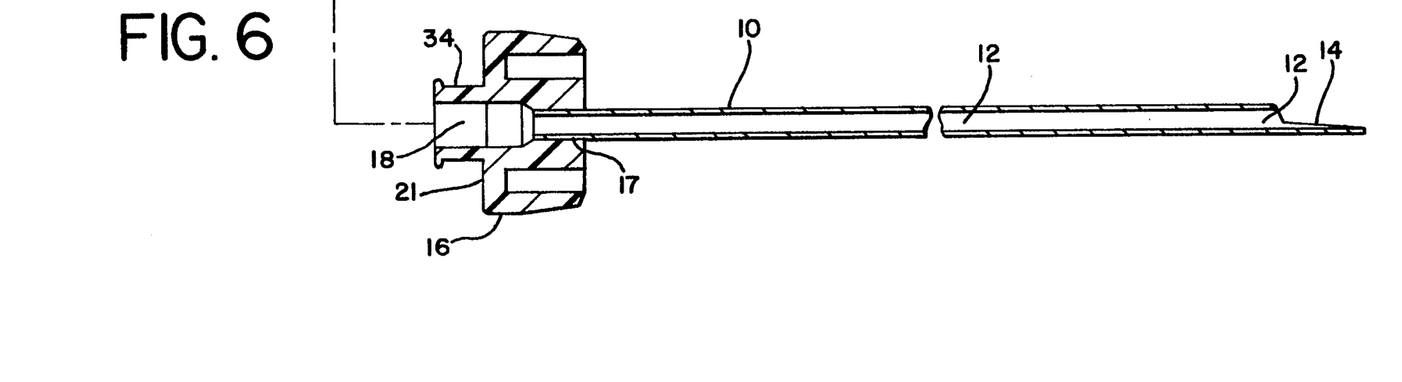
FIG. 6 is a cross-sectional view of the tube and tube handle, said FIGS. 4–6 being a partial exploded view of the assembly of the needle, needle handle, seal housing, tube and tube handle.

Referring to FIGS. 1, 2 and 6, the percutaneous catheter introducer 8 of this invention includes a tube 10 with a lumen 12 of sufficient inside diameter to permit insertion of a catheter that is insertable into an anatomical cavity and a cystic duct for performing a cholangiogram. The wall of the tube is thin so as to minimize the outside diameter of the tube. Preferably, for use with a 5 French catheter, the tube is 304 stainless steel having an inside diameter of approximately 0.0675 inches, an outside diameter of approximately 0.083 inches, and a length of approximately 8.95 inches. The distal tip of the tube is scalloped to make a cut-away tip 14.

A tube handle 16 is located at the proximal end 17 of the tube. The tube handle has an opening 18 which communicates with the lumen 12 in the tube. Preferably, the tube handle is a plastic material.

Figure 3:
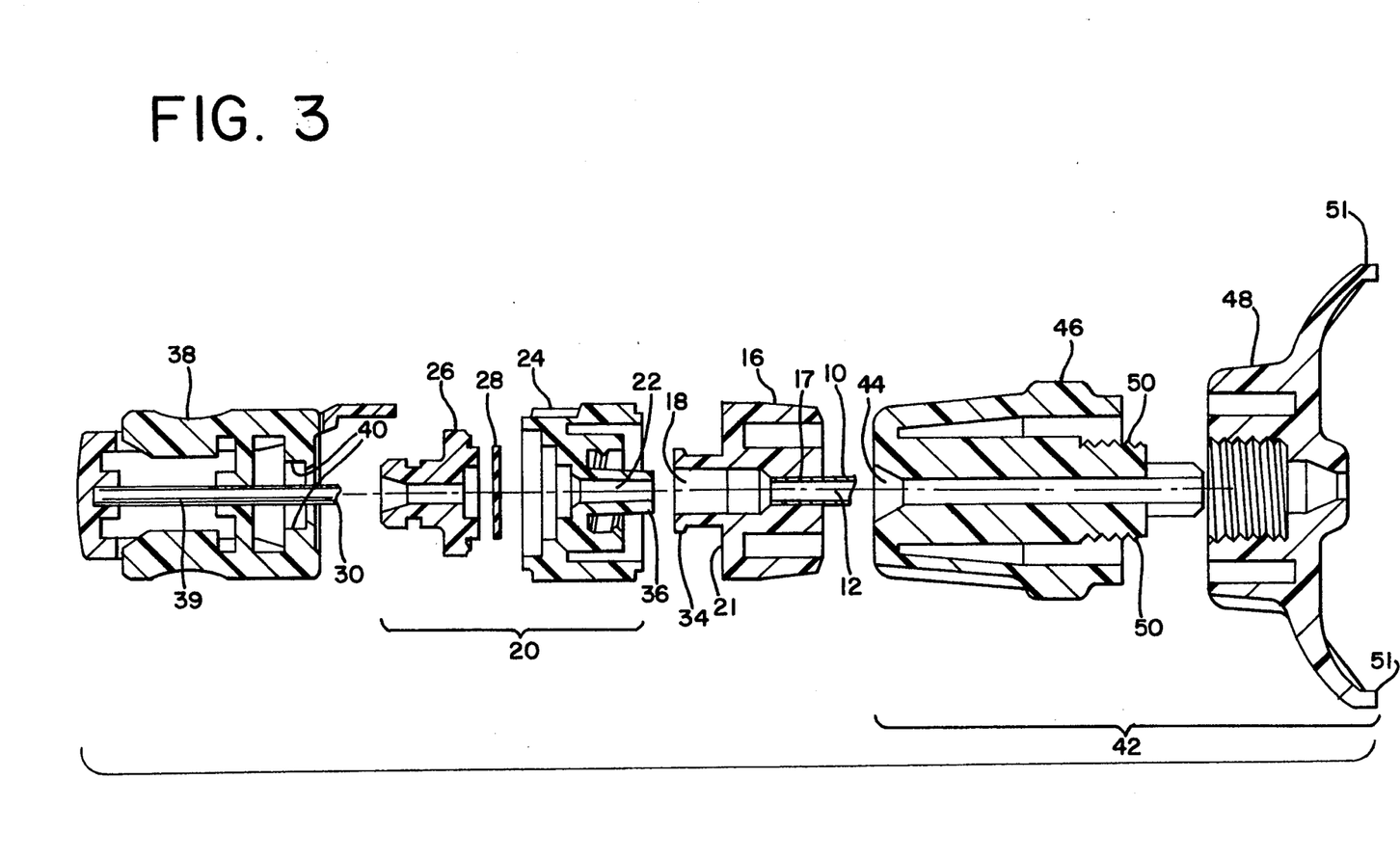
FIG. 3 is a partial exploded cross-sectional view of the percutaneous catheter introducer in accordance with the invention.
Figure 5:
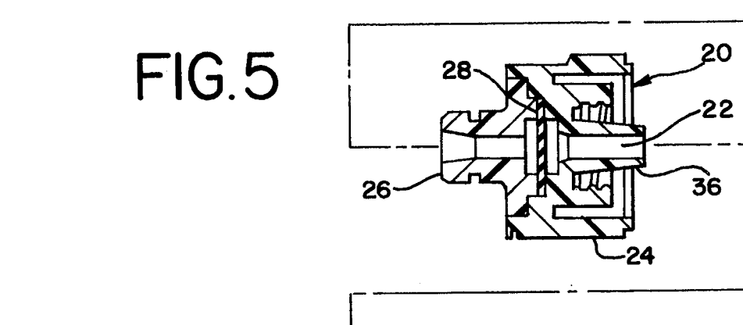
FIG. 5 is a cross-sectional view of the seal housing.

Referring to FIGS. 3 and 5, a seal housing 20 is detachably connected to the proximal end 21 of the tube handle 16. The seal housing defines a passage 22 therein for communicating with the opening 18 in the tube handle 16. Preferably, the seal housing is of two-piece, plastic construction to facilitate ease of assembly. As seen in FIG. 3, the two-piece construction includes a seal holder 24 and a cover 26 fitted thereon.

Figure 7:
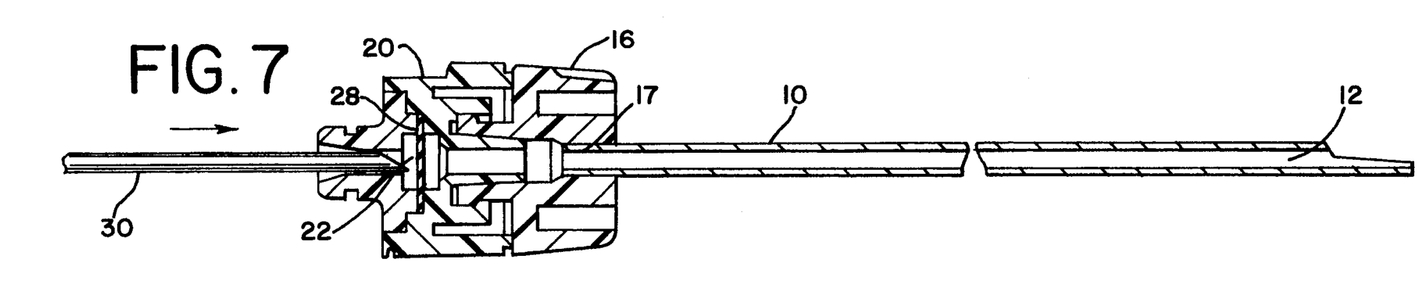
FIG. 7 is a cross-sectional view of the seal housing connected to the tube handle and the needle being inserted into the seal housing.
Figure 8:
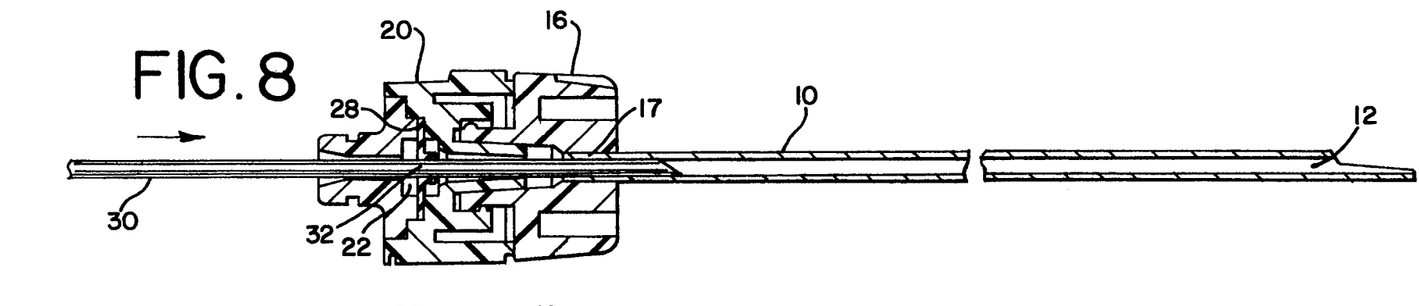
FIG. 8 is a cross-sectional view of the assembly of the seal housing and needle handle with the needle being extended into the seal housing, tube handle and tube.
Figure 9:
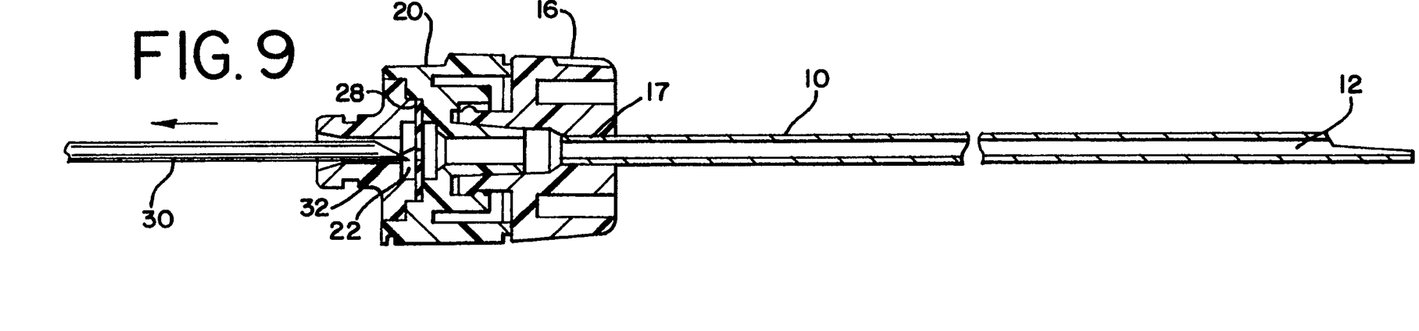
FIG. 9 is a cross-sectional view of the assembly of the seal housing and tube handle shown in FIG. 8 with the needle being withdrawn from the seal housing after it has pierced the seal.

Referring to FIGS. 7-9, a seal 28 extends across the passage 22 in the seal housing 20 so as to obstruct flow of liquid and gas in the passage 22. As shown in FIG. 7, the seal 28 is intact before the needle 30 is inserted into the seal housing 20. As the needle 30 pierces the seal 28 as shown in FIG. 8, the seal 28 contacts the needle 30 and continues to obstruct liquid and gas flow. As the needle pierces the seal, an aperture 32 is created. As shown in FIG. 9, the aperture 32 substantially recloses when the needle is removed and continues to impede liquid and gas flow. Thus, the seal impedes liquid and gas leakage before, during and after it is punctured by a needle. Preferably, the seal is a silicon rubber material in the shape of a round disc.

Figure 14:
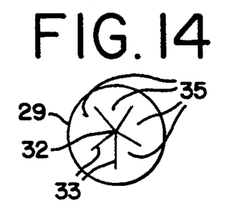
FIGS. 14–16 are plan views of alternative embodiments of a seal with radially extending slits.
Figure 15:
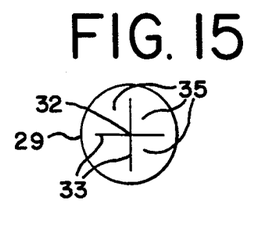
Figure 16:
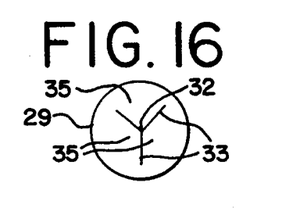

Referring to FIGS. 14-16, in an alternative embodiment according to the invention, a pre-cut seal 29 has a plurality of slits 33 extending radially outward from a central aperture 32. The slits 29 define a series of cusps 35. As installed in the seal housing 20, the cusps 35 have sufficient resilience and rigidity so as to retain a substantially closed configuration as shown in FIGS. 14-16 and thereby substantially impede leakage of liquid and/or gas therethrough. The central aperture 32 permits insertion of a needle 30. The cusps 35 contact the needle and continue to obstruct liquid and gas flow therethrough. When the needle is removed, the cusps return to a substantially closed configuration as shown in FIGS. 14-16.

Figure 17:
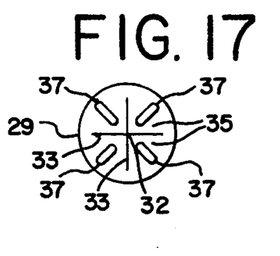
FIG. 17 is a plan view of a seal with radially extending slits and ribs.
Figure 18:
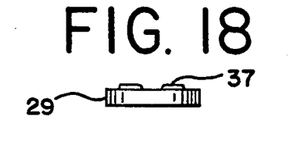
FIG. 18 is an elevational view of the seal shown in FIG. 17.

Referring to FIGS. 17 and 18, an alternative embodiment of the pre-cut seal 29 includes radially-extending reinforcing ribs 37 located on each cusp 35.

Referring to FIG. 3, there is a luer connection provided between the tube handle 16 and the seal housing 20. A female luer fitting 34 extends proximally from the tube handle 16 and a male luer fitting 36 extends distally from the seal housing 20. The luer fittings are threaded so as to be threaded and locked together.

The needle 30 extends through the seal housing 20 and tube 10 as seen in FIG. 2. When fully inserted, the needle tip extends slightly beyond the cut-away tip 14 of the tube 10 as shown in FIG. 1. Preferably, the needle is a stainless steel tube having an outside diameter of approximately 0.065 inches and a length of approximately 10.725 inches.

Figure 4:
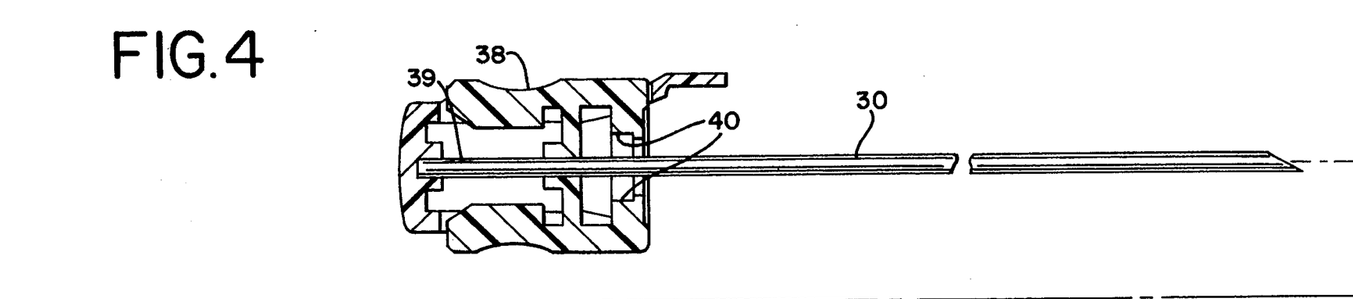
FIG. 4 is a cross-sectional view of the needle and needle handle.

Referring to FIGS. 2-4, a needle handle 38 is connected to the proximal end 39 of the needle 30. Preferably, the needle handle 38 has a squeeze latch 40 which engages the cover 26 of the seal housing 20 so as to detachably connect the needle handle to the proximal end of the seal housing when the needle is fully extended into the tube 10.

Referring to FIGS. 1-3, an adjustable anchor 42 is connected to the tube 10. The anchor has a hole 44 for insertion of the tube so as to permit the anchor to slide along the length of the tube. The anchor is configured to be adjusted to either an anchored configuration wherein the anchor is affixed at a particular location along the length of the tube or a non-anchored configuration wherein the anchor freely slides along the length of the tube.

Preferably, the anchor 42 is a two-piece, plastic construction having male 46 and female 48 portions threaded together. The male portion 46 has a series of fingers 50 which are engaged by the female portion 48. As the male and female portions are rotated relative to each other in one direction, the female portion clamps down on and deflects the fingers of the male portion which in turn grip the tube. In this anchored configuration, the anchor is immobilized and anchored on the tube. When the anchor is in the anchored configuration, depth of insertion of the tube 10 is limited to that length of tube extending distally from the anchor.

As the male 46 and female 48 portions are rotated in the opposite direction, the fingers 50 release their grip on the tube 10. In this non-anchored configuration, the anchor 42 freely slides along the length of the tube. Thus, the anchor is adjustable for setting the depth of insertion of the tube into the body cavity.

Preferably, the anchor 42 has a plurality of feet 51 extending radially outward as shown in FIGS. 1, 10-13. The feet contact the skin 52 and maintain the angle of insertion of the tube 10 (FIG. 10-13).

Referring to FIGS. 7-9, assembly of the percutaneous catheter introducer in accordance with the invention includes connecting the seal housing 20 and tube handle 16 together and inserting the needle 30 through the seal housing 20 and tube handle 16. As the needle is advanced, it pierces the seal 28 so as to make a relatively small aperture 32 therein. Then, referring to FIG. 1, the needle 30 is fully extended into the tube 10 so that its tip extends slightly beyond the cut-away tip 14 of the tube. The needle handle 38 is latched to the seal housing 20. The anchor 42 is fitted on the tube 10 proximally from the cut-away tip 14 in its non-anchored position. At this point, the device 8 is fully assembled and ready for use.

In using the percutaneous catheter introducer 8 described above, a novel method for percutaneous catheter introduction for performing a laparoscopic cholangiogram is practiced, as discussed below.

Figure 10:
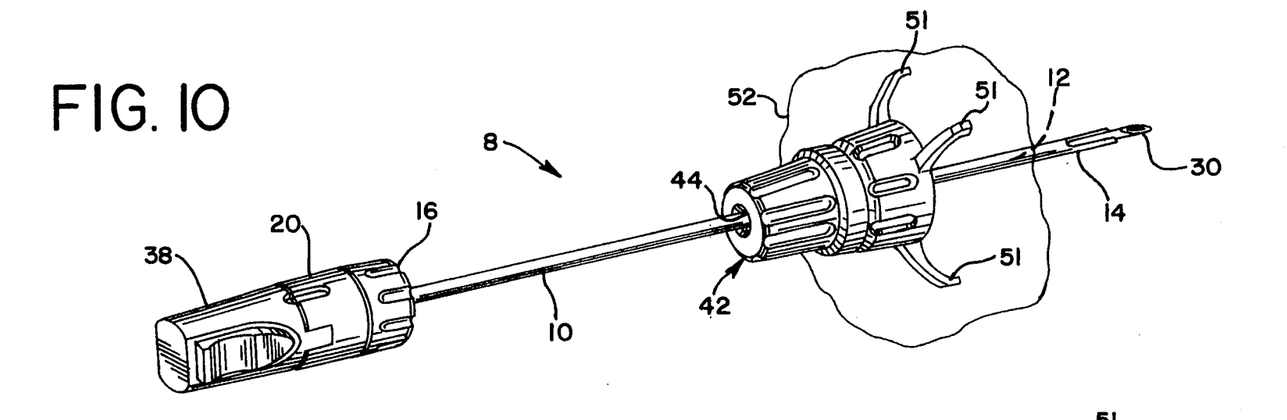
FIG. 10 is a perspective view of the percutaneous catheter introducer in accordance with the invention being inserted into an abdominal body cavity.

Referring to FIG. 10, the assembled device 8 is inserted percutaneously through the skin 52 and abdominal wall into a body cavity. A laparoscope (not illustrated) is inserted in a separate opening in the body cavity in order to view the tube 10 and needle tip as they are inserted into the body cavity.

As the device is inserted, internal fluids and gases enter lumen 12 in the tube 10. The passage of such fluids and gases out of proximal end of the lumen is obstructed by a close fit between the lumen and the needle. To the extent that fluids and gases can flow between the lumen and the needle, such flow is further obstructed by the seal 28 which surrounds the needle 30.

Figure 11:
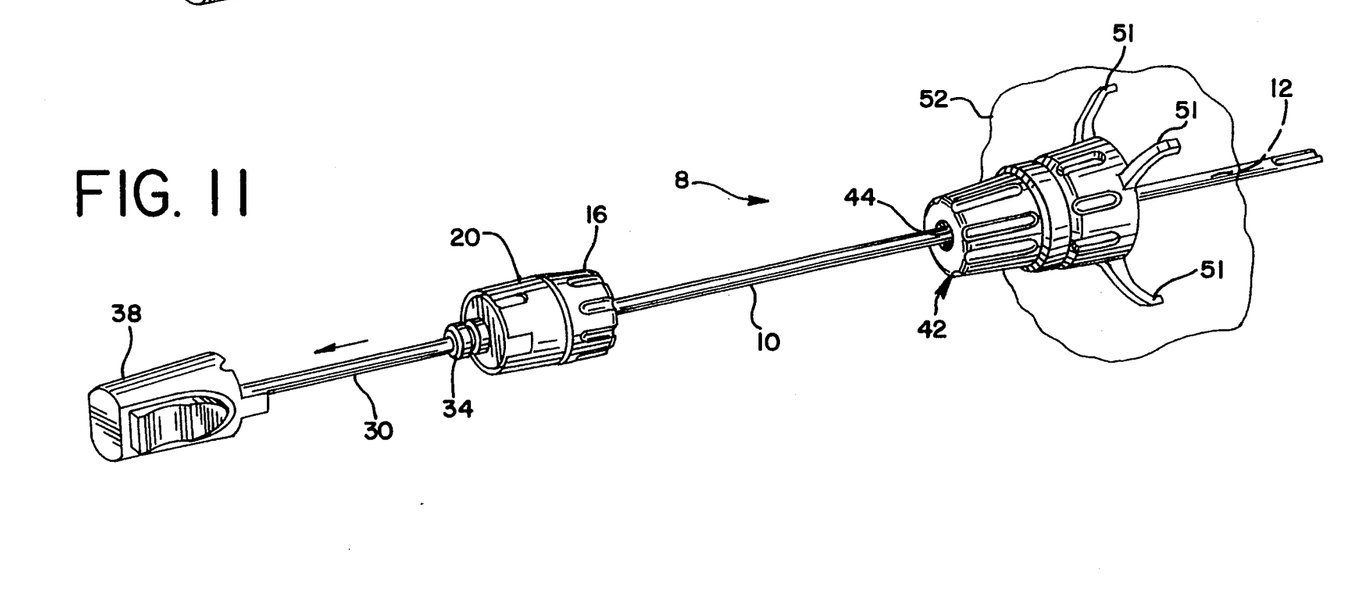
FIG. 11 is a perspective view of the percutaneous catheter introducer in accordance with the invention being inserted into an abdominal body cavity and the needle being withdrawn from the tube.

Referring to FIG. 11, the needle 30 is then unlatched from the seal housing 20 and withdrawn proximally from the tube 10 and seal housing 20 while the tube 10 remains inserted in the body cavity. Then, the tube is positioned next to the cystic duct for guiding a catheter thereinto.

Figures 12, 13:
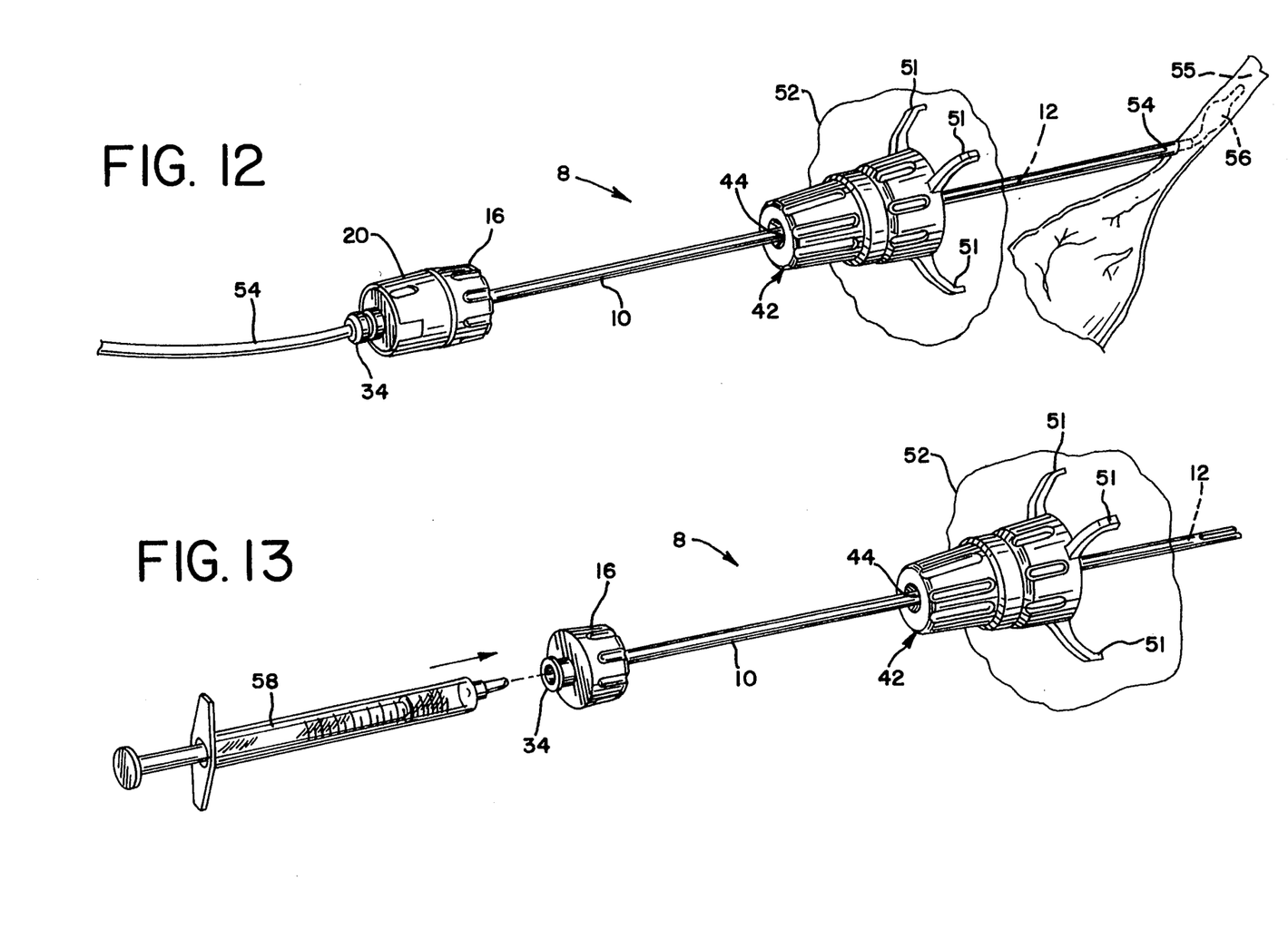
FIG. 12 is a perspective view of the assembly of the seal housing, tube handle, tube and anchor wherein the tube is inserted into an abdominal body cavity and a catheter is extended through the tube and inserted into a cystic duct.
FIG. 13 is a perspective view of the assembly of the tube, handle and anchor being inserted into an abdominal body cavity and a syringe being inserted into the luer fitting in the tube handle.

Referring to FIG. 12, a balloon catheter 54 is inserted into the passage in the seal housing 20. The seal maintains substantial contact with the catheter and continues to obstruct the leakage of liquid and gases from the lumen of the tube 10. The catheter is extended through the lumen, into the body cavity, and into the cystic duct 55. The balloon 56 is inflated inside the cystic duct wherein the injection of radiopaque contract medium, etc. is accomplished.

Alternatively, a non-balloon catheter (not illustrated) is used for insertion into the cystic duct. The non-balloon catheter is stabilized within the cystic duct by conventional means such as a clip that is placed over the cystic duct.

Next, the anchor 42 is slid distally along the tube 10 until it contacts the skin 52 (FIG. 12) and then adjusted or tightened into its anchored configuration. Then, the x-ray is taken.

After the x-ray procedure is completed, the catheter is withdrawn. The tube can then be withdrawn from the body cavity.

In certain procedures, it may be desirable to aspirate materials from an anatomical body cavity using the percutaneous catheter introducer of this invention, such as to aspirate a gall bladder during a cholecystectomy. Aspiration may be accomplished with the apparatus of this invention, as discussed below.

The fully assembled device 8 is inserted percutaneously into an anatomical body cavity adjacent the material to be aspirated. Then, while the tube 10 remains inserted in the body cavity, the needle 30 is withdrawn from the tube 10 and the seal housing 20 is disconnected from the tube handle 16. As shown in FIG. 13, a syringe 58 or other aspirating equipment is connected to the female fitting 34 on the tube handle 16. The material is aspirated through the tube.

Figure 19:
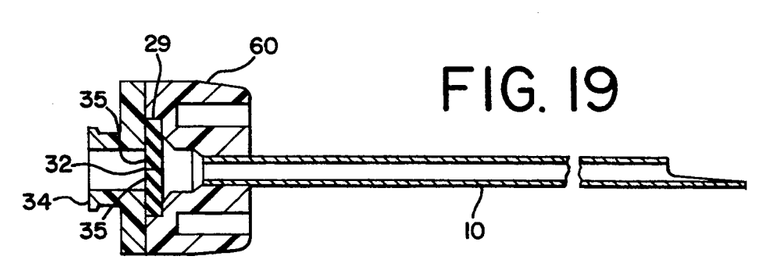
FIG. 19 is a cross-sectional view of an alternative embodiment of the tube and tube handle in accordance with the invention.
Figure 20:
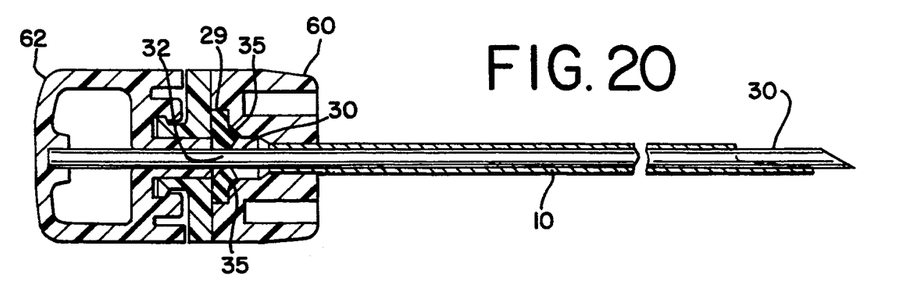
FIG. 20 is a cross-sectional view of an alternative embodiment of the tube and tube handle in accordance with the invention with a needle and needle handle connected thereto.

In an alternative embodiment in accordance with the invention, as shown in FIGS. 19–20, a pre-cut seal 29 having a central aperture 32 is positioned within the tube handle 60 adjacent the proximal end of the tube handle 60 as shown in FIG. 19. A needle 30 is extended through the tube handle 60, seal 29 and tube 10 as shown in FIG. 20. The seal 29 remains in contact with the needle 30 to impede leakage of liquid and/or gas. A needle handle 62 is detachably connected to the tube handle 60 through a luer connection so as to further impede leakage out of the proximal end of the tube 10. When the needle 30 is removed, the seal 29 substantially recloses to its original position as shown in FIG. 19 so as to continue to impede leakage of fluid and/or gas. A catheter is insertable through the central aperture 32 of the seal 29. The seal 29 remains in contact with the inserted catheter so as to impede leakage out of the tube 10. When the catheter is removed, the seal substantially recloses and continues to impede leakage. An anchor (not illustrated) is connected to the tube 10. This alternative embodiment may be used to perform the same cholangiogram procedure discussed above.

Figure 21:
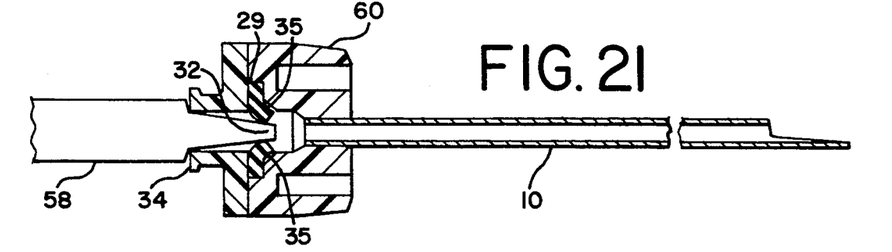
FIG. 21 is a cross-sectional view of an alternative embodiment of the tube and tube handle in accordance with the invention wherein the distal tip of a syringe is inserted into the tube handle.

The alternative embodiment shown in FIGS. 19–21 may be used for aspiration of fluids from an abdominal cavity. Referring to FIG. 21, preferably a syringe 58 is inserted into the female luer fitting 34 extending proximally from the tube handle 60. The distal tip 64 of the syringe 58 deflects the cusps 35 of the seal 29 and extends through the seal 29 so as to bypass the seal. Fluids are then aspirated from the tube into the syringe 58.

Alternatively, fluids may be aspirated from the embodiment shown in FIG. 19 by any aspirating device attached to the proximal end of the tube handle 60. Preferably, the pre-cut seal 29 is of the design shown in FIGS. 14–18 wherein the cusps 35 of the seal 29 will deflect proximally to permit aspiration when suction is applied.

What is claimed is:

1. A percutaneous catheter introducer, comprising:
    a tube defining a lumen for guiding a catheter therethrough and having a proximal end, said tube being percutaneously insertable into an anatomical body cavity for guiding a catheter thereinto;
    a needle extendable through said lumen, said needle having a proximal end;
    a seal housing connected to said proximal end of said tube; and
    a seal positioned within said seal housing, said seal substantially sealing said tube against leakage out of said proximal end of said tube as said needle is extended through said seal and after said needle is removed from said seal, said seal housing being detachable from said tube so as to selectively permit fluid communication through said tube.

2. A percutaneous catheter introducer in accordance with claim 1 wherein said seal permits penetration of said needle so as to make a relatively small aperture therein, said aperture being substantially closed as said needle is removed therefrom.

3. A percutaneous catheter introducer in accordance with claim 2 wherein said aperture permits insertion of a catheter therethrough.

4. A percutaneous catheter introducer in accordance with claim 3 wherein said seal substantially seals said tube against leakage out of said proximal end of said tube as a catheter is extended through said seal and after said catheter is removed from said seal.

5. A percutaneous catheter introducer in accordance with claim 1 wherein said seal defines a central aperture and plurality of radially extending slits.

6. A percutaneous catheter introducer in accordance with claim 5 wherein said central aperture permits insertion of a catheter therethrough, 7. A percutaneous catheter introducer in accordance with claim 6 wherein said central aperture and slits permit aspiration from said proximal end of said tube.

8. A percutaneous catheter introducer in accordance with claim 5 wherein said seal includes at least one reinforcing rib.

9. A percutaneous catheter introducer in accordance with claim 8 wherein said rib is radially extending.

10. A percutaneous catheter introducer in accordance with claim 1 including a tube handle at said proximal end of said tube; said tube handle having a proximal end.

11. A percutaneous catheter introducer in accordance with claim 10 including a luer connection between said tube handle and said seal housing.

12. A percutaneous catheter introducer in accordance with claim 11 including a female luer fitting extending proximally from said tube handle and a male luer fitting extending distally from said seal housing.

13. A percutaneous catheter introducer in accordance with claim 1 including an adjustable anchor assembly connected to said tube for preventing inadvertent increases in the depth of insertion of said tube, said anchor being adjustable to different depths.

14. A percutaneous catheter introducer in accordance with claim 13 wherein said anchor is adjustable between an anchored configuration and a non-anchored configuration, said anchor being affixed to said tube when in said anchored configuration and being longitudinally slidable along the length of said tube when in said non-anchored configuration.

15. A percutaneous catheter introducer in accordance with claim 14 wherein said anchor includes a plurality of feet extending radially outward.

16. A percutaneous catheter introducer in accordance with claim 1 including a needle handle connected to the proximal end of said needle, said needle handle being detachably connected to said seal housing when said needle is extended into said lumen.

17. A percutaneous catheter introducer in accordance with claim 1 wherein said tube includes a cut-away tip.

* * * * *